United States Patent
Dickinson et al.

(10) Patent No.: US 6,458,842 B1
(45) Date of Patent: *Oct. 1, 2002

(54) LIQUID PHARMACEUTICAL COMPOSITIONS COMPRISING THYROID HORMONES

(75) Inventors: Jeffrey Dickinson; Karrar Ahmad Khan; John Neville Hague; Alan Smith, all of Nottingham (GB)

(73) Assignee: Knoll Aktiengesellschaft, Ludwigshafen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/682,779

(22) PCT Filed: Jan. 30, 1995

(86) PCT No.: PCT/EP95/00323

§ 371 (c)(1),
(2), (4) Date: Jul. 31, 1996

(87) PCT Pub. No.: WO95/20955

PCT Pub. Date: Aug. 10, 1995

(30) Foreign Application Priority Data

Feb. 1, 1994 (GB) ................................ 9401891

(51) Int. Cl.[7] ..................... A61K 31/195; A61K 9/08; A61K 47/10
(52) U.S. Cl. ................ 514/567; 514/909; 424/568
(58) Field of Search .................... 514/567; 424/568

(56) References Cited

U.S. PATENT DOCUMENTS

| | | | | |
|---|---|---|---|---|
| 3,090,724 A | | 5/1963 | Bowen | 167/55 |
| 4,766,121 A | * | 8/1988 | Ellis | 514/247 |
| 4,870,106 A | * | 9/1989 | Shihao | 514/567 |
| 4,904,697 A | * | 2/1990 | Sunkara | 514/629 |
| 5,158,978 A | * | 10/1992 | Rubin | 514/567 |
| 5,571,840 A | * | 11/1996 | Mayor | 514/567 |
| 5,635,209 A | * | 6/1997 | Groenewoud | 424/464 |

FOREIGN PATENT DOCUMENTS

| | | |
|---|---|---|
| CA | 680863 | 2/1964 |
| DE | 25 46 474 | 10/1975 |
| GB | 923 171 | 4/1963 |
| GB | 1296510 | 11/1972 |
| GB | 2191695 | 12/1987 |
| JP | 63-79824 | * 4/1988 |

OTHER PUBLICATIONS

Derwent Abst. No. 88–137257, vol. 20, 1988 (English abstract of JP 63079824).

Chem. Abst., vol. 121, No. 18, Abs. No. 213005, Oct. 31, 1994 (English abstract of JP 92–356147).

* cited by examiner

Primary Examiner—Evelyn Mei Huang
(74) Attorney, Agent, or Firm—Lahive & Cockfield, LLP; Peter C. Lauro, Esq.; Giulio A. DeConti, Jr., Esq.

(57) ABSTRACT

There is disclosed a liquid pharmaceutical composition comprising a therapeutic agent which comprises: one or more thyroid hormone or hormones; from about 40% to about 96% ethanol by volume; a pH adjusting agent so that the measured pH of the composition is from about 9 to about 12; and from about 4% to about 50% water by volume; which has utility in the treatment of disorders associated with an impairment of the thyroid hormone function in animals including human beings. The liquid composition may be delivered by a metered dosage delivery system such as an aerosol or pump-action spray.

20 Claims, No Drawings

LIQUID PHARMACEUTICAL COMPOSITIONS COMPRISING THYROID HORMONES

This application is a 371 of PCT/EP95/00323 filed on Jan. 30, 1995.

This invention relates to novel pharmaceutical compositions comprising at least one thyroid hormone and their derivatives, and to their use in the treatment of disorders associated with impairment of the thyroid hormone functions in animals including human beings.

Many patients, particularly the elderly or small children may have difficulty swallowing traditional oral dosage forms. For these patients liquid dosage forms may result in increased patient compliance. Liquid dosage forms may also have the advantage of more reproducible bioavailability over solid dosage forms. However, liquid oral dosage forms (such as solutions, syrups and suspensions) comprising thyroid hormones are difficult to dose accurately due to the small (microgram) quantities of active ingredient. For these reasons products in liquid oral dosage form comprising thyroid hormones are not currently available. Therefore it is an object of the present invention to provide a liquid dosage form and delivery system for thyroid hormone which has improved patient compliance over traditional solid oral dosage forms, which can accurately deliver small doses of thyroid hormone, and which has a suitably long shelf life.

Thyroid hormones comprise one or more of the following:
L-3,5,3', 5'-tetraiodothyronine (levothyroxine or LT4);
L-3,5,3'-triiodothyronine (liothyronine or LT3);
L-3,3', 5,-triiodothyronine (LrT3);
L-3,5-diiodothyronine (LT2); or any mixtures thereof.
As used herein the term thyroid hormone should be understood to include pharmaceutically acceptable salts thereof, preferably sodium salts.

Thyroid hormones as described herein are useful in the treatment of disorders associated with improvement of the thyroid hormone function in animals including human beings for example, myxedema, cretinism or obesity. Thyroid hormones can be prepared synthetically as the biologically active 1-enantiomer or can be isolated directly from the thyroid gland of animals.

Solutions are a highly useful means of administering accurately metered doses of drug substances. However, thyroid hormones are known to be unstable in solution and are not normally sufficiently soluble in water for the intended purpose. Surprisingly, it has been discovered that an ethanolic aqueous solution can form the basis of a stable solution comprising thyroid hormones suitable for use in liquid formulations which can be delivered in metered doses.

Therefore the present invention provides a liquid pharmaceutical composition comprising a therapeutic agent which comprises at least one thyroid hormone; from about 40% to about 96% ethanol by volume; a pH adjusting agent so that the measured pH of the composition is from about 9 to about 12; and from about 4% to about 50% water by volume.

'By volume' throughout the specification and claims indicates a percentage is the volume of a liquid ingredient per total volume of the liquid composition. 'By mass' indicates a percentage is the mass of an ingredient per total mass of the composition.

Thyroid hormones may exist as one or more olymorphic forms (for example one or more crystalline forms, amorphous forms, phases, solid solutions and/or mixtures thereof), and the therapeutic agent may include and pharmaceutically acceptable polymorphic forms of thyroid hormones and/or mixtures thereof.

Thyroid hormones may also exist in the forms of solvates (for example hydrates) and the therapeutic agent may include each solvate of the thyroid hormones and/or mixtures thereof.

Preferably the thyroid hormone is present in the compositions in an amount per unit dose from about 0.1 $\mu$g to about 10,000 $\mu$g, more preferably from about 1 $\mu$g to about 1000 $\mu$g, most preferably if the thyroid. hormone is $LT_4$ from about 25 $\mu$g to about 300 $\mu$g. It will be readily appreciated that the doses of thyroid hormone will vary according to which thyroid hormone or derivative is used and will therefore be adjusted accordingly.

Preferably the volume of the composition per unit dose is about 0.1 $\mu$l to about 10,000 $\mu$l, more preferably from about 1 $\mu$l to about 1,000 $\mu$l, most preferably if the thyroid hormone is $LT_4$ from about 10 $\mu$l to about 600 $\mu$l.

The concentration of thyroid hormone in liquid compositions of the invention will vary according to the unit dose or volume desired and which thyroid hormone derivative is used. However, typically if the thyroid hormone is $LT_4$ the concentration will be from about 0.1 mg $ml^{-1}$ to about 1.0 mg $ml^{-1}$.

Preferably the ethanol is present in an amount from about 50% to about 80%, more preferably from about 60% to about 75%, by volume of the composition.

Preferably the composition further comprises from a trace amount to about 5% by mass of a pharmaceutically acceptable sequestrating agent which may be an ethylene diamine tetra-acetate salt (eg, sodium salt).

Preferably the composition additionally comprises from a trace amount to about 5% by mass of an pharmaceutically acceptable antioxidant which may be a metabisulphite or sulphite salt (eg,a sodium salt).

Preferably the pH adjusting agent is sodium hydroxide and the measured pH of the formulation is from about 9 to about 11, more preferably about 10. It will be readily appreciated by persons skilled in the art that a pH measured in a non-aqueous solvent by a suitable means (for example a pH meter) is not to be considered to relate directly to hydrogen ion concentration but is to be used for comparative purposes only.

The liquid composition of the present invention may further comprise one or more of the following pharmaceutically acceptable optional ingredients:
colouring agents, for example conventional pharmaceutically acceptable dyes;
orally acceptable preservatives, for example benzyl alcohol, sodium hypochlorite, phenoxy ethanol and/or propylene glycol;
sweetening agents for example glycerin, sucrose, sorbitol, sodium saccharin and/or aspartame;
flavouring agents, for example sodium citrate and/or citric acid; and
thickening agents, for example povidone and/or hydroxypropyl methylcellulose.

These optional ingredients may be present in an amount from a trace amount to about 40% by mass of the composition, preferably (if the optional ingredient is other than glycerin) from a trace amount to about 10% by mass.

The formulation of the present invention is suitable for use in a metered dosage delivery system such as a pump-action spray or a pressurised aerosol can, in which the propellent is preferably free of oxygen.

Therefore a further aspect of the invention provides a metered dosage delivery system which comprises a liquid composition as described herein.

A further aspect of the present invention provides use of a thyroid hormone in the preparation of the pharmaceutical compositions described herein for the treatment of disorders associated with an impairment of the thyroid hormone function in animals including human beings.

A still further aspect of the present invention provides a method of treating disorders associated with an impairment of the thyroid hormone function in animals including human beings, which comprises administering to a patient in need thereof a therapeutically and/or prophylactically effective amount of the pharmaceutical compositions described herein.

Whilst the precise amount of the therapeutic agent administered in the treatment described outlined above will depend on a number of factors, for example the severity of the condition, the age and past medical history of the patient, and always lies within the sound discretion of the administering medical practicner or veterinary a suitable daily dose of a thyroid hormone for administration to animals, preferably human beings, may generally be from about 0.1 μg to about 10,000 μg, preferably from about 1 μg to about 1,000 μg, more preferably if the thyroid hormone is $LT_4$ from about 25 μg to about 300 μg, given in a single dose or in divided doses at one or more times during the day.

Liquid compositions of the present invention provide a versatile means in which to administer a unit dose of the therapeutic agent. For example when the therapeutic agent is $LT_4$, the liquid dosage form may comprise a spray or aerosol comprising a solution having a concentration of $LT_4$ of 1 mg $ml^{-1}$. Preferably the spray delivers a volume of solution per unit dose of from about 25 μl to about 300 μl (equivalent to a dose of from about 25 μg to about 300 μg). If the spray comprises a solution having a concentration of $LT_4$ of 0.5 mg $ml^{-1}$ then preferably the spray delivers a volume of solution per unit dose of from about 50 μl to 600 μl (equivalent to a dose of from about 25 μg to about 300 μg of $LT_4$).

Pharmaceutical compositions of the present invention may be used in adjunctive therapy with one or more other compounds having activity in the treatment of disorders associated with an impairment of the thyroid hormone function in animals including human beings. It will be appreciated that the term treatment as used herein includes prophylactic use of the pharmaceutical compositions of the present invention, for example to protect against conditions such as hypothyroidism, in animals including human beings.

The invention will now be illustrated by the following non-limiting examples. Throughout the examples % m/v indicates the percentage in the amount of ingredient by mass (g) per volume of the composition (ml) and % v/v indicates the percentage in the amount of ingredient by volume.

EXAMPLE 1

| Ingredient | % m/v | |
|---|---|---|
| Levothyroxine sodium ($LT_4$) | 0.1 | |
| EDTA (Sequestrene NA4) | 0.05 | |
| Sodium metabisulphite | 0.05 | |
| Sodium saccharin | 0.10 | |
| Ethanol | 70 | (% v/v) |
| Purified water to . . . | 100 | |

The above ingredients were mixed together to form an ethanolic solution which had a pH, measured with a pH meter, of 9.3. The solution was filtered and sealed in ampoules, the headspace being air.

The stability of the therapeutic agent ($LT_4$) in this formulation was tested with the formulation held at various temperatures over 6 months. The results are tabulated below, as a fraction of $LT_4$ remaining. A dash indicates that no data are available for the amount of $LT_4$ present at a particular temperature after a particular duration.

| Temp °C. | Initially | Duration | | | | |
| | | After 2 weeks | 1 month | 2 months | 3 months | 6 months |
|---|---|---|---|---|---|---|
| 4 | 0.97 | — | — | 0.99 | 1.00 | 1.09 |
| 25 | 0.97 | 1.01 | 1.00 | 0.99 | 1.00 | 1.07 |
| 30 | 0.97 | — | — | 0.99 | — | 1.07 |
| 40 | 0.97 | — | — | — | 0.97 | 1.00 |
| 50 | 0.97 | 1.03 | 0.94 | — | 0.88 | 0.81 |

EXAMPLES 2 TO 3

| Ingredient | % m/v | |
|---|---|---|
| Levothyroxine sodium ($LT_4$) | 0.1 | |
| EDTA (Sequestrene NA4) | 0.05 | |
| Sodium sulphite | 0.05 | |
| Glycerin | 30.0 | (% v/v) |
| Ethanol | 40.0 | (% v/v) |
| Purified water to . . . | 100 | |

The above ingredients were mixed to form a solution as in Example 1, which had a pH, measured with a pH meter, of 9.3. The stability results over 3 months for this solution filled into ampoules having either an air (Example 2) or nitrogen (Example 3) headspace are given in the following table, as a fraction of $LT_4$ remaining.

| Temp °C. | Initially | Duration | | |
| | | 1 month | 2 months | 3 months |
|---|---|---|---|---|
| Example 2 - Ampoule (air) | | | | |
| 4 | 0.97 | 0.99 | 0.99 | 0.97 |
| 25 | 0.97 | 0.98 | 0.98 | 0.95 |
| 40 | 0.97 | 0.99 | 0.95 | 0.80 |
| 50 | 0.97 | 0.97 | 0.83 | 0.68 |
| Example 3 - Ampoule (nitrogen) | | | | |
| 4 | 0.98 | 0.99 | 1.00 | 0.97 |
| 25 | 0.98 | 0.99 | 0.99 | 0.97 |
| 40 | 0.98 | 0.98 | 0.98 | 0.95 |
| 50 | 0.98 | 0.99 | 0.96 | 0.93 |

EXAMPLES 4 TO 6

| Ingredient | % m/v | |
|---|---|---|
| Levothyroxine sodium | 0.1 | |
| EDTA (Sequestrene NA4) | 0.05 | |
| Sodium sulphite | 0.05 | |
| Ethanol | 70 | (% v/v) |
| Purified water to . . . | 100 | |

The above ingredients were mixed to form a solution as in Example 1, which had a pH, measured with a pH meter, of 10.1. The stability results are tabulated below in a similar manner to Examples 1 to 3 above for a solution filled into ampoules and having an air (Example 4) or a nitrogen (Example 5) headspace. Stability results for a solution prepared as above (with a measured pH of 10.0) which was filled into a pump pack (Example 6) is also given in the following table. A ash indicates no data are available.

|  | Duration | | | | |
|---|---|---|---|---|---|
| Temp °C. | Initially | 1 month | 2 months | 3 months | 6 months |
| Example 4 (ampoule - air) | | | | | |
| 4 | 1.01 | 0.99 | 1.0 | 0.99 | 0.98 |
| 25 | 1.01 | 1.00 | 0.95 | 0.99 | 0.99 |
| 40 | 1.01 | 0.99 | 0.99 | 0.97 | 0.94 |
| 50 | 1.01 | 0.96 | 0.95 | 0.89 | 0.84 |
| Example 5 (Ampoule - nitrogen) | | | | | |
| 4 | 1.01 | 1.04 | 1.01 | 1.01 | 1.00 |
| 25 | 1.01 | 1.00 | 1.01 | 0.99 | 1.00 |
| 40 | 1.01 | 1.00 | 1.01 | 0.99 | 1.00 |
| 50 | 1.01 | 0.99 | 0.99 | 0.96 | 0.95 |
| Example 5 (Pump pack) | | | | | |
| 4 | 1.02 | 1.03 | — | 1.03 | — |
| 25 | 1.02 | 1.04 | — | 1.04 | — |
| 40 | 1.02 | 1.01 | — | 1.05 | — |
| 50 | 1.02 | 1.00 | — | 0.99 | — |

EXAMPLES 7 TO 9

| Ingredient | % m/v |
|---|---|
| Levothyroxine sodium | 0.1 |
| EDTA (Sequestrine NA4) | 0.05 |
| Sodium sulphite | 0.1 |
| Ethanol | 70 (% v/v) |
| Purified water to . . . | 100 |

The above ingredients were mixed as in Example 1 to produce a solution with a measured pH of 10.3, which was then stored as described in Examples 4 to 6. The stability results are 5 as follows. A dash indicates no data are available.

|  | Duration | | | | |
|---|---|---|---|---|---|
| Temp °C. | Initially | 1 month | 2 months | 3 months | 6 months |
| Example 7 (Ampoule - air) | | | | | |
| 4 | 1.00 | 0.99 | 1.01 | 1.01 | 1.00 |
| 25 | 1.00 | 0.99 | 1.00 | 0.99 | 0.98 |
| 40 | 1.00 | 0.98 | 0.99 | 0.96 | 0.97 |
| 50 | 1.00 | 0.96 | 0.965 | 0.91 | 0.86 |
| Example 8 (Ampoule - nitrogen) | | | | | |
| 4 | 1.01 | 0.99 | 1.01 | 1.00 | 1.01 |
| 25 | 1.01 | 0.99 | 1.01 | 1.00 | 1.00 |
| 40 | 1.01 | 0.99 | 1.00 | 1.00 | 1.01 |
| 50 | 1.01 | 0.99 | 1.01 | 0.99 | 0.97 |
| Example 9 (Pump pack) | | | | | |
| 4 | 1.03 | 1.02 | — | 1.02 | — |
| 25 | 1.03 | 1.02 | — | 1.03 | — |
| 40 | 1.03 | 1.03 | — | 1.04 | — |
| 50 | 1.03 | 1.01 | — | 0.99 | — |

EXAMPLE 10 TO 12

| Ingredient | % m/v |
|---|---|
| Levothyroxine sodium | 0.1 |
| EDTA (Sequestrene NA4) | 0.05 |
| Sodium sulphite | 0.1 |
| Sodium saccharin | 0.1 |
| Ethanol | 70 (% v/v) |
| Purified water to . . . | 100 |

The above ingredients were mixed as in Example 1 to produced a solution with a measured pH of 10.2 and 10.3, which was then stored as described in Examples 4 to 6. The stablity results are as follows. A dash indicates no data are available.

|  | Duration | | | | |
|---|---|---|---|---|---|
| Temp °C. | Initially | 1 month | 2 months | 3 months | 6 months |
| Example 10 (Ampoule - air) | | | | | |
| 4 | 0.95 | 1.04 | 0.95 | 0.95 | 0.97 |
| 25 | 0.95 | 1.04 | 0.96 | 0.92 | 0.94 |
| 40 | 0.95 | 1.03 | 0.95 | 0.90 | 0.93 |
| 50 | 0.95 | 1.00 | 0.90 | 0.83 | 0.81 |
| Example 11 (Ampoule - nitrogen) | | | | | |
| 4 | 0.96 | 1.05 | 0.96 | 0.97 | 0.97 |
| 25 | 0.96 | 1.06 | 0.99 | 0.93 | 0.95 |
| 40 | 0.96 | 1.06 | 0.97 | 0.93 | 0.98 |
| 50 | 0.96 | 1.06 | 0.97 | 0.91 | 0.92 |
| Example 12 (Pump pack) | | | | | |
| 4 | 0.99 | 1.04 | — | 0.99 | — |
| 25 | 0.99 | 1.03 | — | 1.00 | — |
| 40 | 0.99 | 1.05 | — | 0.99 | — |
| 50 | 0.99 | 1.02 | — | 0.95 | — |

What is claimed is:

1. A stable liquid oral dosage pharmaceutical composition, said composition comprising at least one thyroid hormone selected from the group consisting of L-3,5,3',5'-tetraiodothyronine (levothyroxine or LT4), L-3,5,3'-triiodothyronine (liothyronine or LT3), L-3,3',5'-triiodothyronine (LrT3), L-3,5-diiodothyrone (LT2), pharmaceutically acceptable salts thereof, and mixtures thereof; from about 40% to about 96% of ethanol by volume; a pH adjusting agent so that the measured pH of the composition is from about 9 to about 12; and from about 4% to about 50% water by volume.

2. A composition as defined in claim 1, in which the ethanol is present in an amount from about 50% to about 80% by volume of the composition.

3. A composition as defined in claim 1, which further comprises from a trace amount to about 5% by mass of the composition of a pharmaceutically acceptable sequestrating agent.

4. A composition as defined in claim 1, which further comprises from a trace amount to about 5% by mass of the composition of a pharmaceutically acceptable anti-oxidant.

5. A method of treating a disorder associated with an impairment of the thyroid hormone function in a mammal, which method comprises administration to a mammal in need of such treatment a therapeutically effective amount of the stable liquid oral dosage pharmaceutical composition defined in claim 1.

6. A method of preparing a stable oral liquid dosage pharmaceutical composition as defined claim 1, which method comprises combining the thyroid hormone with from about 40% to about 96% of ethanol by volume; and from about 4% to about 50% water by volume; and then adjusting the pH of the resulting solution to a pH of from about 9 to about 12.

7. A method as defined in claim 6, in which the ethanol is added to the composition in an amount from about 50% to about 80% by volume of the composition.

8. A method as defined in claim 7, which further comprises adding to the composition from a trace amount to about 5% by mass of the composition of a pharmaceutically acceptable sequestrating agent.

9. A method as defined in claim 6, which further comprises adding to the composition from a trace amount to about 5% by mass of the composition of a pharmaceutically acceptable anti-oxidant.

10. A composition as defined in claim 1, wherein the fraction of the initial thyroid hormone concentration in the composition remaining after storage of the composition at 25° C. in air for 6 months is at least 0.94.

11. A composition as defined in claim 1, wherein the fraction of the initial thyroid hormone concentration remaining after storage of the composition at 25° C. under nitrogen for 6 months is at least 0.95.

12. A composition as defined in claim 1, wherein the thyroid hormone is L-3,5,3',5'-tetraiodothyronine (levothyroxine or LT4) or a pharmaceutically acceptable salt thereof.

13. A composition as defined in claim 1, wherein the thyroid hormone is L-3,5,3'-triiodothyronine (liothyronine or LT3) or a pharmaceutically acceptable salt thereof.

14. A composition as defined in claim 1, wherein the thyroid hormone is L-3,3',5'-triiodothyronine (LrT3) or a pharmaceutically acceptable salt thereof.

15. A composition as defined in claim 1, wherein the thyroid hormone is L-3,5-diiodothyronine (LT2) or a pharmaceutically acceptable salt thereof.

16. A method as defined claim 6, wherein the thyroid hormone is L-3,5,3',5'-tetraiodothyronine (levothyroxine or LT4) or a pharmaceutically acceptable salt thereof.

17. A method as defined in claim 6, wherein the thyroid hormone is L-3,5,3'-triiodothyronine (liothyronine or LT3) or a pharmaceutically acceptable salt thereof.

18. A method as defined in claim 6, wherein the thyroid hormone is L-3,3',5'-triiodothyronine (LrT3) or a pharmaceutically acceptable salt thereof.

19. A method as defined in claim 6, wherein the thyroid hormone is L-3,5-diiodothyronine (LT2) or a pharmaceutically acceptable salt thereof.

20. A method as defined in claim 5, wherein the mammal is a human.

\* \* \* \* \*